US005505691A

United States Patent [19]

Fenkell

[11] Patent Number: 5,505,691

[45] Date of Patent: Apr. 9, 1996

[54] THERAPEUTIC TREATMENT MACHINE

[76] Inventor: Randall Fenkell, 6850 NW. 2nd Ave. #35, Boca Raton, Fla. 33487

[21] Appl. No.: 166,847

[22] Filed: Dec. 15, 1993

[51] Int. Cl.[6] .......... A61F 5/00

[52] U.S. Cl. .......... 601/99; 601/98; 601/116; 606/241; 606/242

[58] Field of Search .......... 601/97, 98, 99, 601/115, 116, 126, 101, 102, 103, 104, 24, 26; 606/237, 240, 241, 242, 243, 244

[56] References Cited

U.S. PATENT DOCUMENTS

| | | | |
|---|---|---|---|
| 1,098,327 | 5/1914 | Koch . | |
| 1,280,987 | 10/1918 | Gregory | 606/241 |
| 1,593,014 | 7/1926 | Bushmiller . | |
| 1,643,040 | 9/1927 | Wentz . | |
| 1,748,425 | 2/1930 | Odell . | |
| 2,230,057 | 1/1941 | Hill . | |
| 2,262,271 | 11/1941 | DeCamp | 601/26 |
| 2,534,587 | 12/1950 | Fisher et al. . | |
| 2,693,796 | 11/1954 | Warner | 606/242 |
| 2,781,040 | 2/1957 | Hill . | |
| 2,819,713 | 1/1958 | Buck | 601/98 |
| 2,822,805 | 2/1958 | Hill . | |
| 2,874,689 | 2/1959 | Gavelek . | |
| 2,949,911 | 8/1960 | Kennard | 601/26 |
| 3,164,150 | 1/1965 | Reid . | |
| 3,238,936 | 3/1966 | Siedentop . | |
| 3,445,205 | 5/1969 | Minohara . | |
| 3,830,233 | 8/1974 | Hill . | |
| 3,835,844 | 9/1974 | Lang . | |
| 4,144,880 | 3/1979 | Daniels | 606/242 |
| 4,154,232 | 5/1979 | Fukazawa . | |
| 4,230,098 | 10/1980 | Uematsu . | |
| 4,579,109 | 4/1986 | Lundblad | 606/242 |
| 4,856,497 | 8/1989 | Westphal | 606/242 |
| 4,860,734 | 8/1989 | Lyu . | |
| 4,890,604 | 1/1990 | Nelson . | |
| 5,297,539 | 3/1994 | Liebl | 601/26 |

FOREIGN PATENT DOCUMENTS

| | | |
|---|---|---|
| 2477870 | 3/1980 | France . |
| 1491277 | 8/1963 | Germany . |

*Primary Examiner*—Robert A. Hafer
*Assistant Examiner*—David J. Kenealy

[57] ABSTRACT

A therapeutic treatment machine for alternatingly applying equal amounts of compression and traction to the body of a patient includes a platform having an upper body support pad with selectively controllably resistance to forward and backward displacement, rotatable rollers to support the lower back, buttocks and thighs of the patient, and a selectively controllable motor driven foot support platform displaceable forward and backward predetermined distances and speeds. The distance between the upper body support pad and the foot support platform is adjustable to accommodate differences in patient torso lengths and the magnitude of compressive and tractional force can be selectively controlled by the patient.

9 Claims, 7 Drawing Sheets

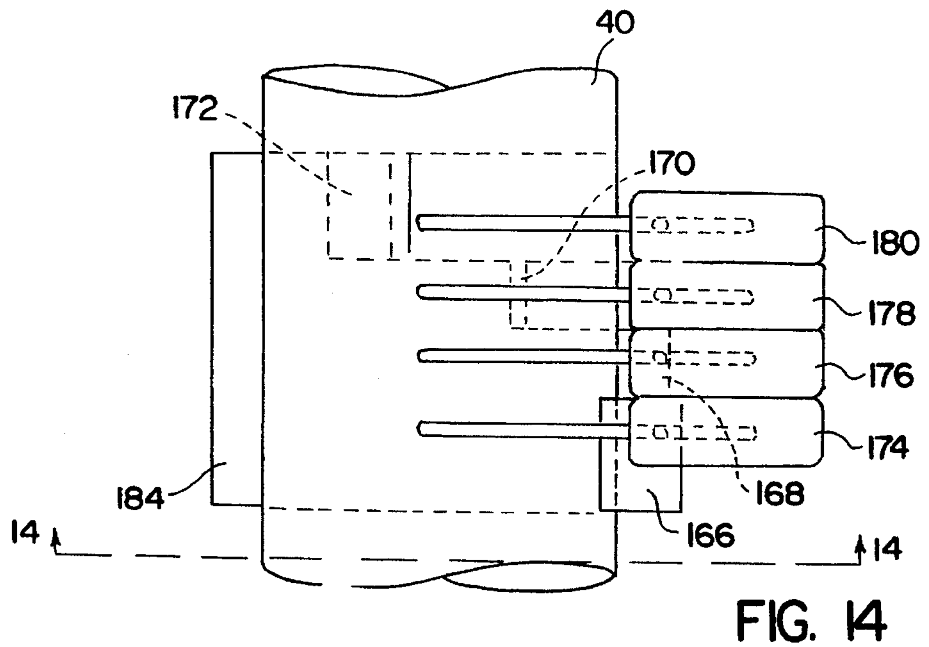
FIG. 14
FIG. 15
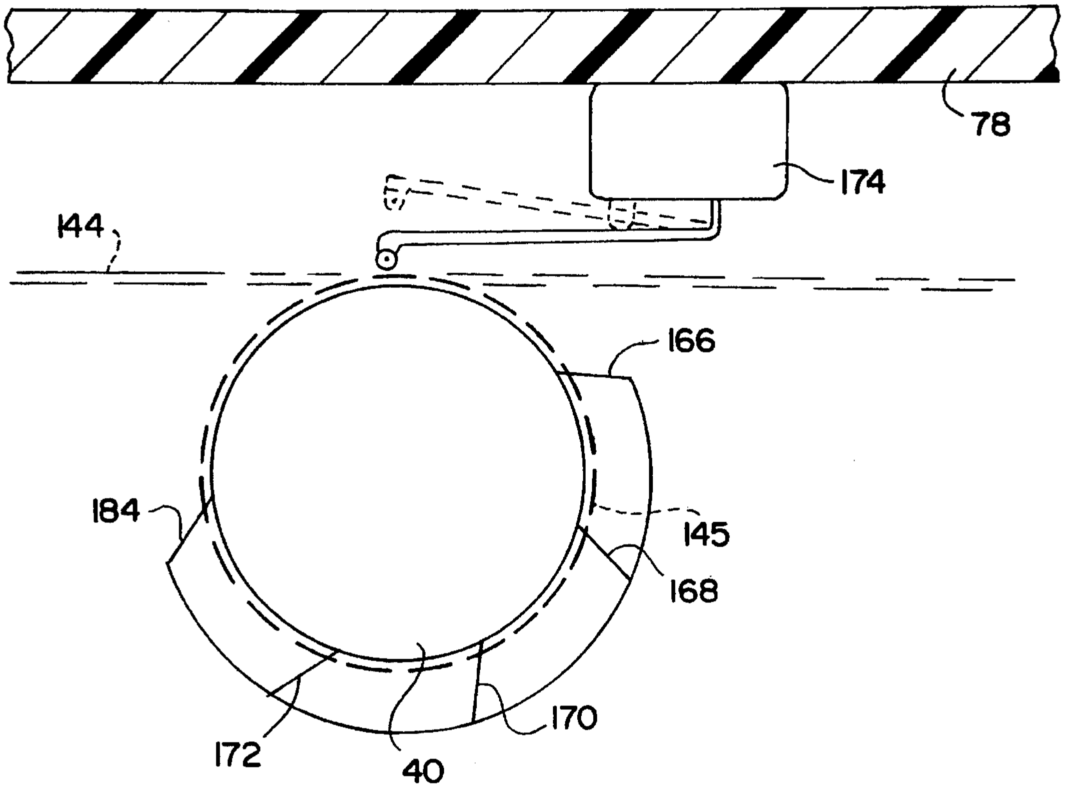

THERAPEUTIC TREATMENT MACHINE

BACKGROUND OF THE INVENTION

1. Field of the Invention

The present invention relates to methods and apparatus for therapeutically treating the human body and, more particularly, to a method and apparatus for relieving discomfort and pain in the back, spine and neck of a human patient.

2. Discussion of the Prior Art

More than seventy-five million Americans suffer from chronic back pain and a third of the entire population experiences some minor back pain. The most common approach to attempt to provide relief from such pain and related inflammation is to try to increase the flow of blood to the affected area by periodic applications of traction and relaxation. Devices, generally in the form of tables on which a patient lies, are used to apply tension to the human body to relieve pressure on bones, muscles, cartilage and the like. Massaging members, frequently in the form of rollers over which the patient's body moves, are included in some such devices along with means for applying heat and vibration. Exemplary of such devices is the treatment table described in U.S. Pat. No. 3,830,233 (Hill) which shows a table having a stationary support section and a movable adjacent section reciprocated by an electric motor to provide alternating periods of traction and relaxation between portions of the body supported by the two sections. Timers and limit switches are included to control duration and extent of tensioning, rollers protrude through the table to provide massaging pressures to the patient and heat and vibration can be applied for additional effect. Another approach, exemplified by a tilting traction table disclosed by U.S. Pat. No. 4,890,604 (Nelson), fixedly supports the head and feet of a patient on a platform with the major trunk portion of the patient resting on a slidable platform. The table is inclined to allow gravity acting on the weight of the patient to apply tension, or traction, to the back and spine. Some such treatment tables provide a degree of relief from conditions and symptoms exacerbated by continual normal pressure, as for instance spasms, backaches and pinched nerves resulting from various spinal column irregularities; however, the duration and scope of relief leave something to be desired. After studying the matter I came to realize that during the traction stroke the pelvis tilts forward towards the feet causing extension of the lumbar spine. This increase in the lumbar lordosis causes compression of the posterior elements which can cause the disk material to extend further into the area carrying the nerves coming from the spinal column and that the relaxation portion of the tension-relaxation cycle produces no beneficial results. In fact, the Medical Profession has, for the most part, abandoned traction therapy and it is used mostly to immobilize a person with back problems to allow the body the heal itself.

OBJECTS AND SUMMARY OF THE INVENTION

Accordingly, the primary object of the present invention is to provide a method and apparatus for therapeutic treatment of a patient by converting the counter-productive relaxation phase of the prior art traction-relaxation cycle to a phase having therapeutic value. In particular, it is an object of the invention to provide repetitive cycles of traction and compression phases to parts of a patient's body.

Another object of the present invention is to provide a method and apparatus for automatically inducing a traction and compression cycle of preselected duration and intensity in the back, spine and neck of a patient.

It is another object of the present invention to provide a therapeutic treatment method and apparatus capable of inducing posterior tilting of the pelvis during a compression cycle to decrease lumbar lordosis (i.e., the inward curvature of the spine), relax posterior elements of the spine and compress anterior elements.

Yet another object of the present invention is to provide a therapeutic treatment method and apparatus allowing the patient to adjust the amount of tension and compression applied cyclically to a treated body part.

Still another object of the present invention is to provide repetitive and cyclical applications of equal amounts of tension and compression to the back, spine and neck of a patient.

Some of the advantages of the present invention over the prior art are that: by adding compression to traction we make both phases of the traction-compression cycle therapeutically beneficial; the patient is able to control and vary the intensity and duration of the traction-compression therapy; and the apparatus is simple and inexpensive to manufacture and can be fabricated in a compact and portable embodiment suitable for use by travelers.

In accordance with the present invention a treatment table has a longitudinally slidable upper body pad for supporting the upper back, shoulders and head of a supine patient, freely rotatable transversely extending rollers for supporting the lower back, buttocks and thighs of the patient, and a selectively controlled, motor driven, movable platform adapted to engage the feet of the patient. A reversible electric motor longitudinally reciprocates the movable foot platform a preselected distance, adjustable by the patient, to sequentially and repetitively place the patient in tension and compression. The table is easily deployed for use and is optimally collapsible into a unit that is easily hand-carried by a patient while travelling.

Other objects and advantages of the present invention will become apparent from the following description of the preferred embodiment taken in conjunction with the accompanying drawings wherein like reference numerals in the various figures represent like components.

BRIEF DESCRIPTION OF THE DRAWINGS

FIG. 14 is a partial top view in plan of the stroke length selection and reversing mechanism of FIG. 12; and FIG. 15 is a view in section taken along lines 15—15 of FIG. 14.

DESCRIPTION OF THE PREFERRED EMBODIMENTS

Figure 1:
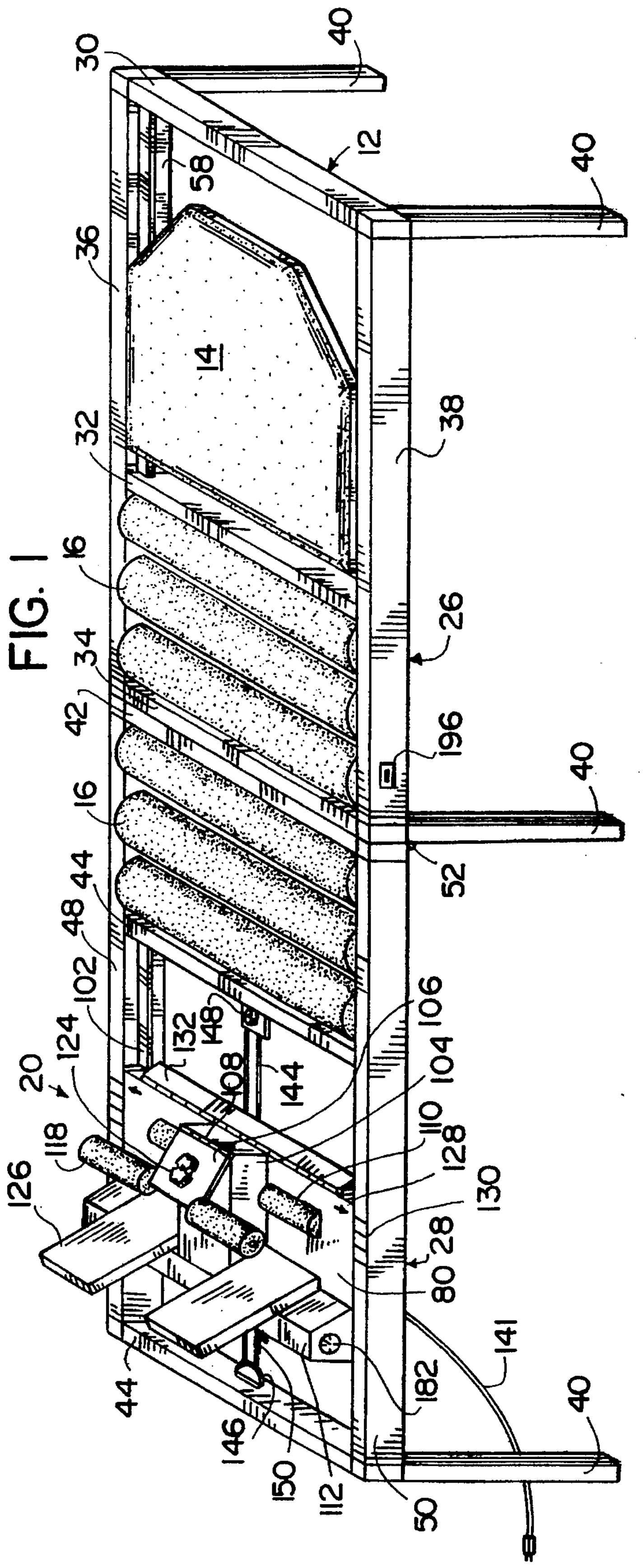
FIG. 1 is a view in perspective of the therapeutic treatment machine of the present invention.
Figure 2:
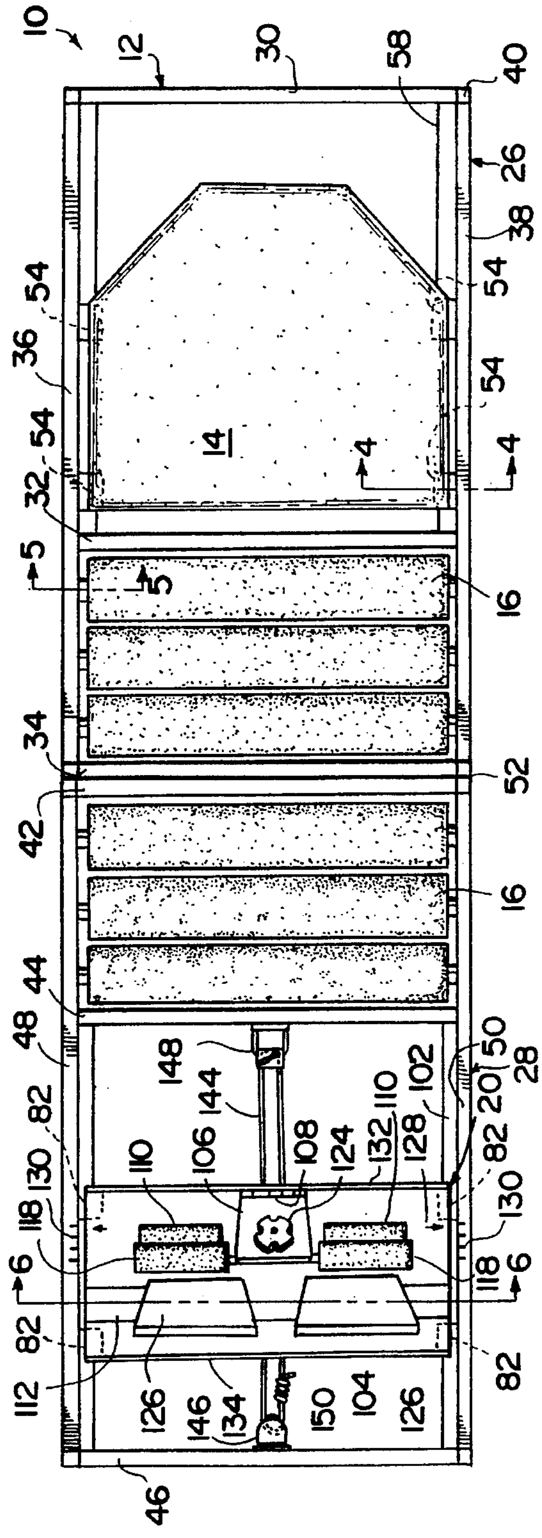
FIG. 2 is a top view in plan of the machine of FIG. 1.
Figure 3:
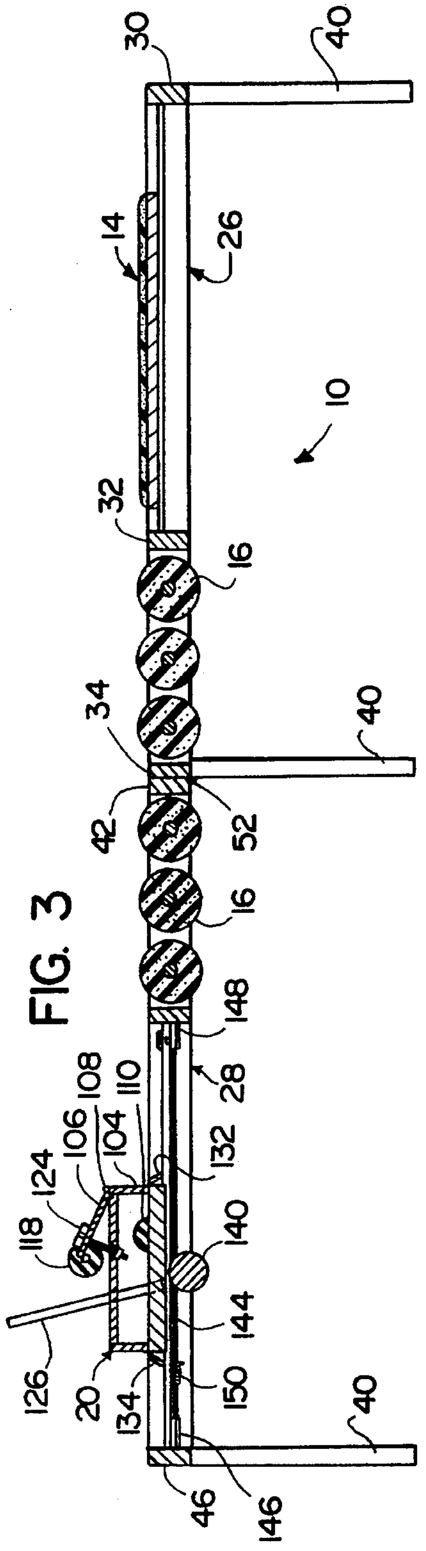
FIG. 3 is a side elevation view in partial section of the machine of FIG. 1.

A therapeutic treatment machine 10 according to the present invention, shown in FIGS. 1 through 3, includes a rectangular table frame 12 supporting an upper body pad 14, located toward the front of the table, a series of freely rotatable massage rollers 16 located toward the middle of the table and a motor driven, selectively reciprocating foot support platform 20 located toward the back of the table. Rectangular frame 12 is made of, for instance, aluminum angle or tube, and has a forward frame section 26 housing the upper body pad 14, and a rearward frame section 28 of similar size and shape housing the foot support platform 20. Forward section 26 has a forward end 30, a rearward end 34 and a transverse support member 32 extending parallel to the ends 30, 34 between right and left sides 36 and 38, respectively, when viewed from the forward end. Table legs 40 support the therapeutic treatment machine at a convenient height for ease of use (e.g. twenty to twenty-four inches) and extend downward from the four corners of forward frame section 26. Rearward frame section 28 also has a forward end 42, a rearward end 46 and a transverse support member 44 extending parallel to ends 42 and 46 between right and left sides 48 and 50 respectively. Table legs 40 extend downward from the back corners of rearward frame section 28. Table legs 40 are removably attached to frame 12 for ease and compactness of storage and may be conveniently but removeably locked into frame 12 with spring-loaded detents of conventional design. Forward frame section rearward end 34 is connected along the lower surface to the lower surface of rearward frame section forward end 42 by a hinge 52 to allow the two sections to be folded together for portability and storage compactness.

Figure 4:
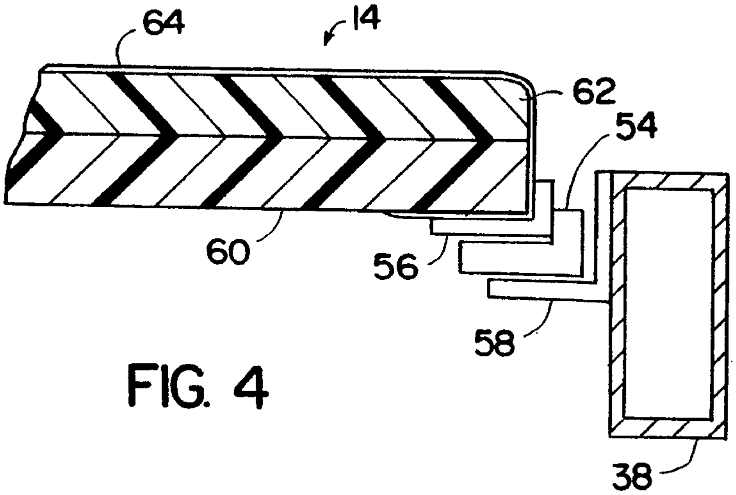
FIG. 4 is a view in section taken along lines 4—4 of FIG. 2.

Friction bearings 54 of, for instance, Teflon, mounted on sections of aluminum channel 56, are attached to the underside of the upper body pad 14 as shown in FIG. 4 and are slidably mounted in angle stock 58 attached along the inner surfaces of forward frame section sides 36 and 38. Resistance to movement of upper body pad 14 along angle stock 58 is proportional to the weight exerted on the pad and is equal in the forward and rearward direction. The forward and rearward displacement or stroke of the upper body pad along angle stock 58 is limited by the forward end 30 of the forward frame section 26 and transverse support member 32. The upper body pad comprises a plywood deck 60 with foam rubber 62 or other resilient padding material affixed to the upper surface and covered with a durable material 64 offering frictional resistance to the head, shoulders and upper back of the patient.

Figure 5:
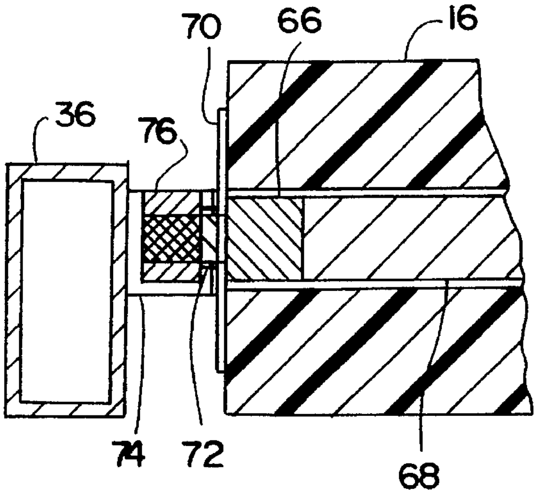
FIG. 5 is a view in section taken along lines 5—5 of FIG. 2.

Rollers 16 of conventional design partially extend above the forward frame section 26 between transverse support member 32 and rearward end 34, and above the rearward frame section 28 between forward end 42 and transverse support member 44. The rollers are rotatably mounted to opposite sides of the frame by bronze pins 66, shown in FIG. 5, extending from the axles 68 of the rollers, through washers 70, through holes 72 drilled in the inner surfaces of aluminum channel 74 attached to the inner surfaces of frame sides 36, 38, 48 and 50, and into bearings 76 press-fit into the channels.

Figure 6:
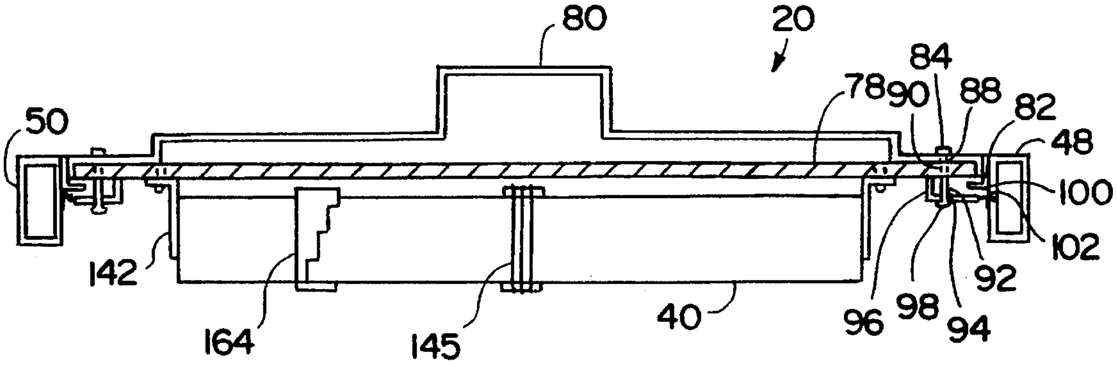
FIG. 6 is a view in section taken along lines 6—6 of FIG. 2.
Figure 7:
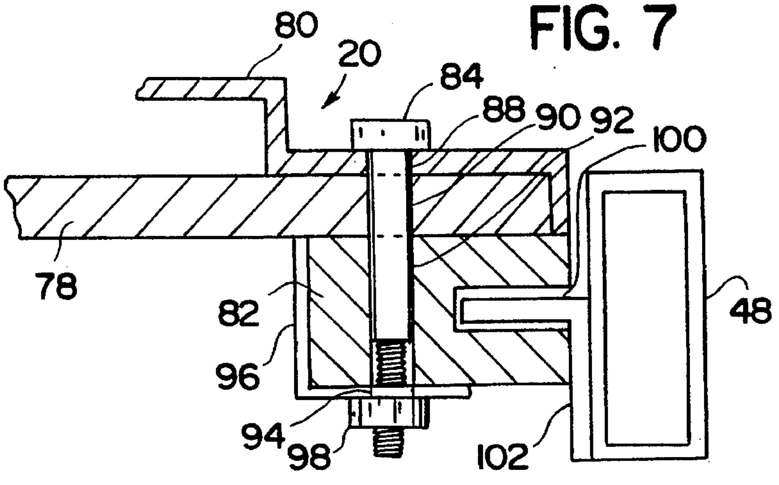
FIG. 7 is a partial cross-section of a foot support platform bearing block assembly slidingly supported by a table side.

Foot support platform 20, shown in detail in FIGS. 6 and 7, has a rectangular plywood base 78 sized to fit horizontally between rearward frame section sides 48 and 50. A molded foot rest assembly 80 is attached to the upper surface of base 78. Bearing blocks 82 of, for instance, Teflon, are held against the lower surface of each corner of base 78 by bolts 84 passing through holes 88 in foot rest assembly 80, holes 90 in base 78, holes 92 in bearing blocks 82 and holes 94 in sections 96 of aluminum angle and threadingly received by nuts 98. Slots 100 formed in the outer surfaces of bearing blocks 82 receive the horizontal leg of angle stock 102 rigidly attached to the inner surfaces of frame sides 48 and 50 to slidingly support foot support platform 20 in the table frame 12.

Figure 8:
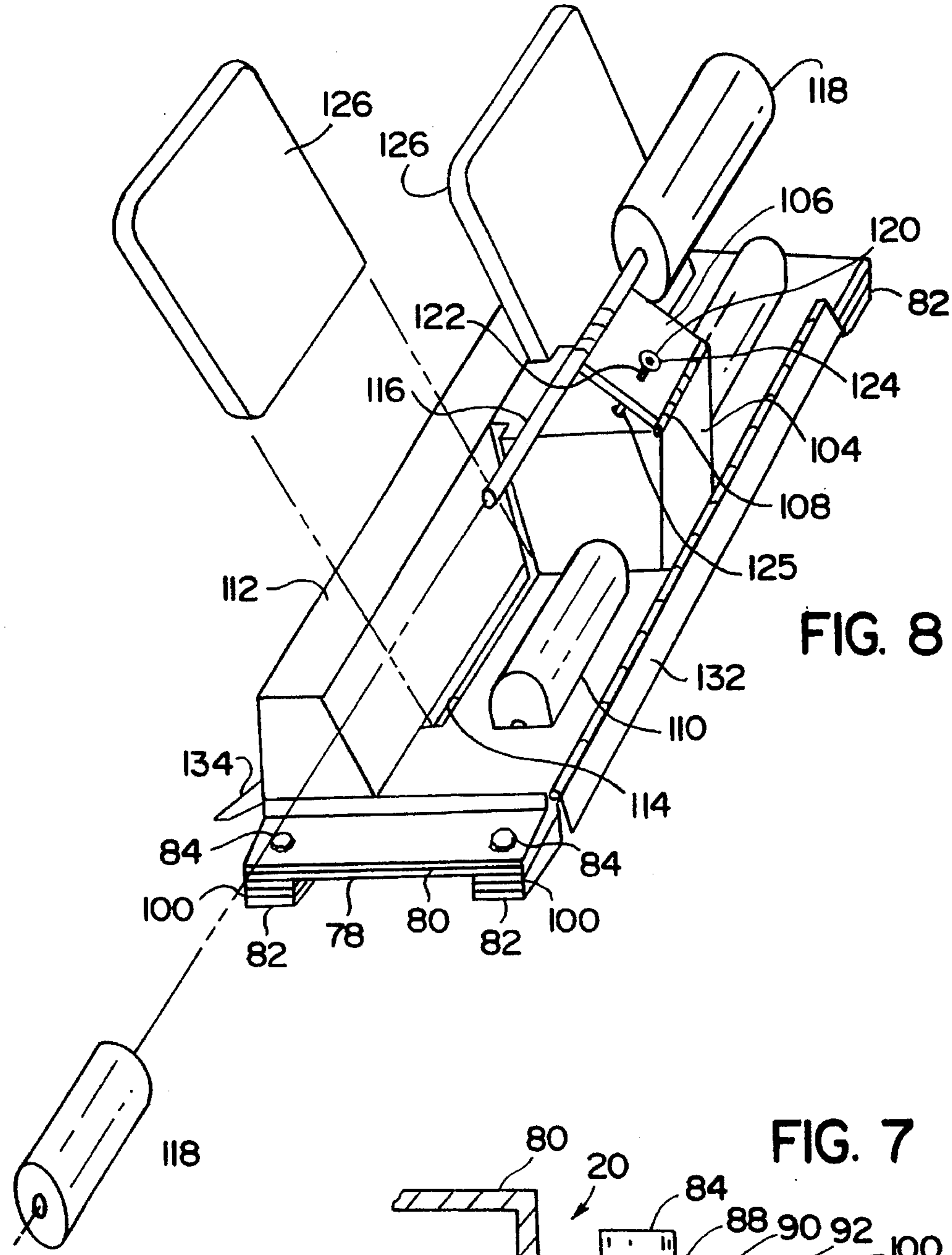
FIG. 8 is a perspective view of the foot support platform with left foot plate and left padded foot clamp removed.

The molded foot rest assembly 80, shown in detail in FIG. 8, is attached to the top of plywood base 78 and has a central console box 104 extending along its central front portion. A plate 106 is rotatably and removeably attached to the top front of console box 104 by means of a detachable hinge 108. Padded heel rests 110 are disposed on either side of console box 104, and a foot plate support box 112 extends transversely across the top of base 78 behind console box 104. Lateral slots 114 are provided on opposite sides of console box 104 directly forward of foot plate support box 112.

Plate 106 has a horizontal crossbar or rod 116 rigidly attached along its back or non-hinged end with padded foot clamps 118 secured to each end of the rod. A stud handle 120, extends downward through plate 106 and consists of a threaded bolt 122 and an attached rotatable knob 124 permanently and rotatably attached to plate 106. Threaded bolt 122 is received in threaded engagement with hole 125 in console box 104 and tightened by rotation of knob 124 to adjustably limit the distance foot clamps 118 can be rotated away from platform 20. The slots 114 adjacently forward of the foot plate support console are sized to removably receive and support flat foot plates 126 in a generally upright position braced by support box 112. Foot plates 126 and plate 106 are detachable for compact storage and portability.

Positioning arrows 128 (FIGS. 1 and 2) are inscribed on the upper sides of the molded foot rest assembly to align with a series of marks 130 inscribed along frame sides 48 and 50 to indicate various separation distances between the upper body pad 14 and foot support platform 20 corresponding to various patient torso lengths.

Figure 9:
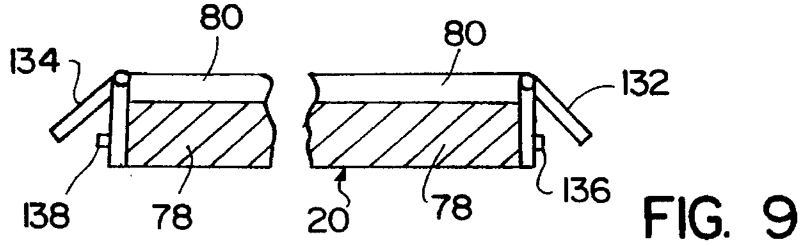
FIG. 9 is a broken elevation view in partial section of the front and rear safety switch and activating hinge mechanisms.

As shown in FIG. 8, hinges 132 and 134 are mounted on the front and rear edges, respectively, of foot support platform 20 and are spring biased in a partially open position. As seen in detail in FIG. 9, safety stop microswitches 136 and 138 are mounted on the front and rear edges, respectively, of foot support platform 20 and are activated by the rotational closing of the hinges in response to a body part or other obstruction closing the hinge by blocking the unimpeded forward or backward movement of the foot support platform within frame 12. Activation of either microswitch causes the platform reciprocation to immediately stop, as is described more fully below, to prevent accidental injuries.

Figure 10:
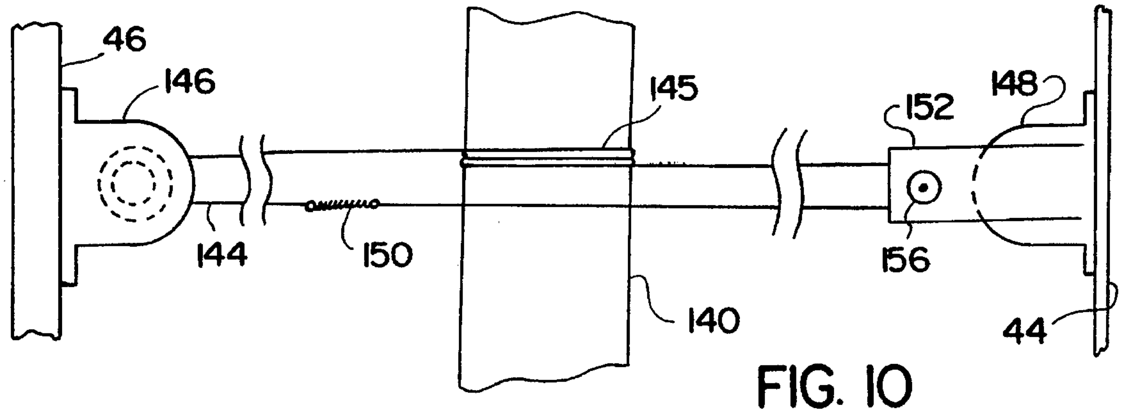
FIG. 10 is a broken view in plan of a drive cable path.
Figure 11:
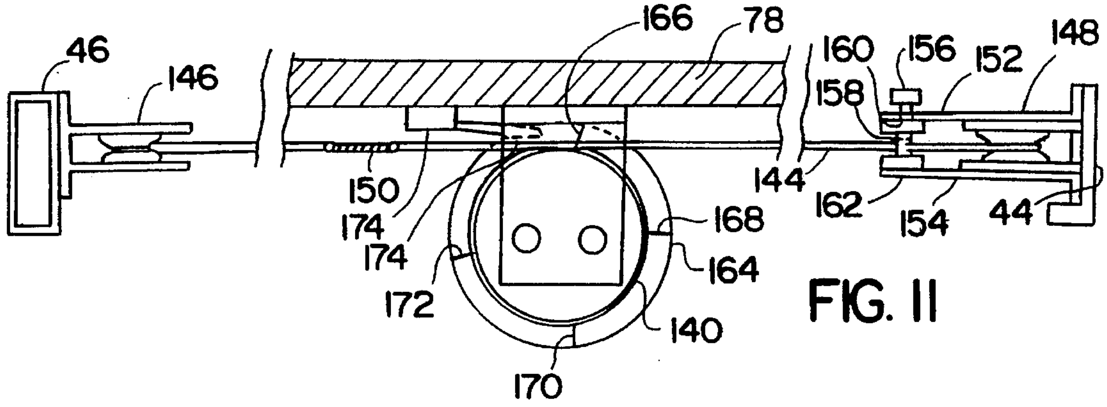
FIG. 11 is a broken elevation view of the cable path.
Figure 12:
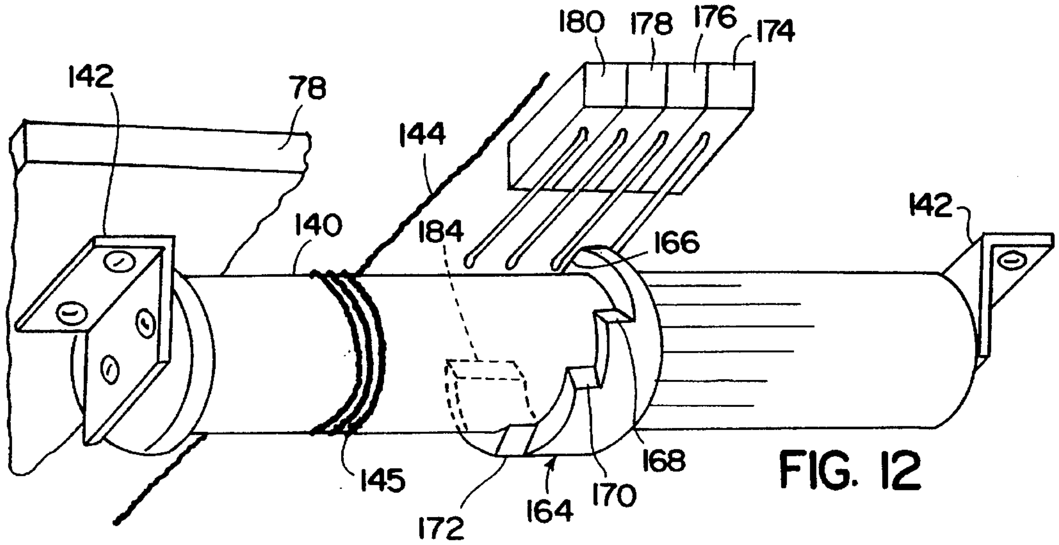
FIG. 12 is a perspective view of a stroke length selection and reversing mechanism of the present invention.

Referring now to FIGS. 10, 11 and 12, a tubular motor 140 (for example DC powered tubular operator reference model 535.113 marketed by SIMU, B.P.72-Arc-Les-Gray, 70103

Gray Cedex, France) is energized by a.c. convenience power passing through on-off switch 196 (FIGS. 1 and 13) in series with a.c. line cord 141, and is mounted across the lower surface of plywood base 78 with brackets 142 (FIG. 12). A drive cable 144 frictionally (i.e., non-slidingly) engages tubular motor 140 in one or more loops 145 and passes through a rear horizontal roller or pulley assembly 146 mounted on the inner surface of the rearward end 46 of rearward frame section 28 and a forward horizontal roller assembly 148 mounted on the back surface of transverse support member 44. A turnbuckle 150 connects the two ends of drive cable 144 to form a continuous loop around the motor and the two roller assemblies. Cable 144 passes between upper and lower cantilevered clamping arms 152 and 154 respectively extending rearward from forward roller assembly 148. A knob 156 having a threaded axle 158 is positioned at the end of arms 152 and 154 with axle 158 passing through a hole 160 in upper arm 152 and received in threaded hole 162 in lower arm 154. Rotation of knob 156 to advance axle 158 into threaded hole 162 urges arms 152 and 154 together to clamp drive cable 144.

A notched or stepped partial cylinder 164, shown in FIG. 12, 14 and 15 is tightly fitted around tubular motor 140. The leading edges of the steps are located at different longitudinal positions along cylinder 164 and are circumferentially displaced by distances corresponding to desired strokes or lengths of linear displacement (i.e., in the forward and rearward direction) of the foot support platform 20. A nearly complete revolution of a two inch diameter tube motor results in about a six inch linear displacement of the platform. The leading step edges 166, 168, 170 and 172 of the steps, spaced to provide linear displacements, pushes and pulls, of, for instance, three, four, five and six inches, are aligned with the lever arms of corresponding snap-acting switches 174, 176, 178 and 180, respectively, and each of the switches is in turn connected to a displacement selection rotary control 182 (FIGS. 1 and 13) having separate manually selected positions permitting the patient to select which one of switches 174, 176, 178 or 180 is active. As the tubular motor 140 rotates in a first direction, counterclockwise as illustrated in FIGS. 12, 14 and 15 the leading edges 166, 168, 170 and 172 progressively actuate the corresponding snap switches 174, 176, 178 and 180, respectively. Only engagement of the selected or active switch (i.e., the one selected by manual control 182) completes a circuit to signal a bistable impulse relay 192 to reverse the direction of rotation of the tube motor, and consequently the direction of linear displacement of the foot support platform. Reversal of rotation direction of tubular motor 140 also disengages the activated snap switch immediately and then each of the previously actuated switches in turn. As the tube continues to rotate, now in a second direction, clockwise as pictured in FIG. 12, the trailing edge 184 (FIG. 12) of the stepped partial cylinder 164 simultaneously engages all of the snap switches, including the switch activated by rotary control 182, once again signalling the impulse relay to reverse the direction of rotation, thereby beginning the cycle anew and performing one complete cycle in, for instance four to ten seconds. The linear displacement of the foot support platform corresponds to the circumferential distance from the leading edge 166, 168, 170, 172 rendered active by rotary control 182 to the trailing edge 184. The speed or pace of the reciprocating displacements is a function of the tube motor rotation speed.

Figure 13:
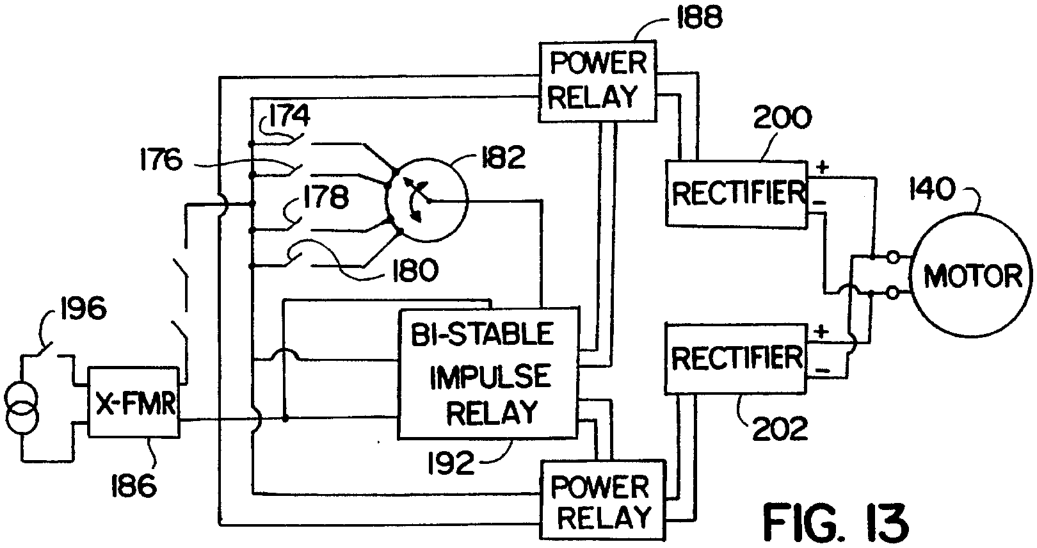
FIG. 13 is an electrical schematic diagram of the stroke length control circuit.

FIG. 13 shows the circuit diagram for the tube motor stroke selection control. Alternating current is stepped down to twelve volts by transformer 186. One side of the reduced a.c. voltage line is passed through safety switches 136 and 138 connected in series and then through the parallel combination of snap-action switches 174, 176, 178, 180. The other sides of these snap-action swatches are connected to respective input terminals of rotary control 182. The output terminal of control 182 is connected as one control line to a bistable impulse relay 192, the control line being derived from the unswitched reduced a.c. voltage line from transformer 186.

The reduced a.c. voltage lines from transformer 186, one of which passes through safety switches 136, 138, are applied as input power lines to bistable impulse relay 192 and, after rectification, to each of two power relays 188 and 190. Bistable impulse relay 192 may be from the S89R/S90R series manufactured by Potter and Brumfield. Input power lines to relay 188 are derived from a rectifier 200 which converts the a.c. voltage to a d.c. voltage. Input power lines to relay 190 are derived from a similar rectifier 202. Rectifiers 200 and 202 provide d.c. voltage through respective relays 188, 190 to motor 140 in opposite polarities so that when relay 188 is active it drives the motor in one direction, and when relay 190 is active it drives the motor in the opposite direction.

Power relays 188 and 190 are controlled by respective output line pairs from bistable impulse relay 192. Specifically, when the selected one of snap-action switches 174, 176, 178, 180 is actuated, the bistable impulse relay 192 is temporarily energized. One pair of a.c. output voltage lines becomes and remains active and energizes power relay 188; relay 190 is not energized at this time. When the bistable impulse relay is again energized (i.e., when the selected one of switches 174, 186, 178, 180 is actuated again), the other pair of a.c. output voltage lines from relay 192 becomes active and energizes power relay 190; relay 188 is not energized at this time. It will be appreciated, therefore, that the rotation direction of motor 140 depends on whether or not bistable impulse relay 192 is energized and that the energization state of relay 192 depends upon whether or not one of the snap-action switches 174, 176, 178 and 180 is closed.

In use a patient first positions upper body pad 14 midway between the forward end and transverse support member 30 and 32, respectively, of forward frame section 26, then loosens knob 156 to disengage clamping arms 152 and 154 allowing drive cable 144 to move freely around roller assemblies 146 and 148. Foot support platform 20 is positioned to accommodate the torso length of the patient by aligning arrows 128 with one of the positioning marks 130. Knob 156 is tightened to clamp drive cable 144 between arms 152 and 154 and the patient lies supine on the table with head, shoulders and upper back resting on upper body pad 14 and lower back and buttocks resting on rollers 16. Plate 106 is rotated upward and the patient's feet are inserted under foot clamps 118, with the bottoms of the feet pressed against foot plates 126 and the backs of the feet resting on heel rests 110. Plate 106 is rotated back downward and threaded bolt 122 is inserted into hole 125 in console box 104 and tightened by rotation of knob 124 to comfortably secure the feet in position between the heel rests and foot clamps.

The length of displacement in the forward and backward direction applied to the patient by the machine, the pushing and pulling, respectively, of the foot support platform, 20, toward and away from upper body pad 14, is selected by setting rotary control 182 to activate one of the snap switches 174, 176, 178 or 180. The therapeutic treatment machine is then energized by turning on-off switch 196 to the "on" position. Tubular motor 140 rotates, taking up drive cable 144 in one direction and simultaneously releasing cable in the opposite direction, driving the tubular motor and consequently the foot support platform 20 along angle stock 102 attached along frame sides 48 and 50, supported and guided by slots 100 in bearing blocks 82. As motor 140 rotates, stepped partial cylinder 164, attached thereto, rotates as well with leading edges 166, 168, 170 and 172 progressively activating snap acting switches 174, 176, 178 and 180. When the switch selected by rotary control 182 is engaged bistable impulse relay 192 is energized to reverse the direction of rotation of tubular motor 140. Drive cable 144 is taken up in the opposite direction reversing the direction of travel of foot support platform 20, disengaging the selected snap acting switch, and each other switch in turn until the trailing edge 184 of the stepped partial cylinder 164 simultaneously engages all of the snap switches once again completing the circuit through the selected switch to the bistable impulse relay to once again reverse the direction of rotation of tubular motor 140 and the forward or backward direction of displacement of foot support platform 20.

The weight or force exerted by the head, shoulders and upper back of the patient on the upper body pad 14 controls the frictional resistance to sliding developed between friction bearings 54 and angle stock 58 and is equal in the forward and rearward direction. When the compression or tension force transmitted through the body of the patient by the reciprocating foot support platform exceeds the frictional force between the friction bearings and the angle stock, the upper body pad will slide along the table frame to relieve and prevent additional force from being carried by the body. Consequently the patient can control the magnitude of tension and compression forces applied by the therapeutic treatment machine by increasing or decreasing the amount of body weight applied to the upper body pad. The platform continues to cycle back and forth applying alternating compression and traction to the patient until turned off at on-off switch 196 or until an encounter with an obstruction by one of the hinges 132 and 134 mounted on the front and back, respectively, of foot support platform 20 activates a safety stop microswitch.

During compression posterior tilting of the pelvis takes place decreasing lumbar lordosis, relaxing the posterior elements of the spine and compressing the anterior elements. During traction the pelvis tilts forward causing extension of the lumbar spine. The increase in lumbar lordosis causes compression of the posterior elements and traction of the anterior elements.

When the treatment is concluded the machine can be partially dismantled for compact storage or ease of portability by removing legs 40 and hinged plate 106 and folding forward section 26 and rearward section 28 together around hinge 52.

A timer can be included in the circuitry to allow the user to preset a duration for traction-compression cycling. The rate can be controlled by using a variable rpm tube motor and selective delays can be incorporated into the cycle to hold a traction, compression or relaxation phase for desired periods of time. A microprocessor based controller can be used to program the nature and duration of treatment. Furthermore, a simple ice bath of conventional design can effectively be incorporated into the roller apparatus to provide further therapeutic action or alternatively, the rollers can be replaced by a temperature controllable waterbag having low sliding resistance to allow the patient's mid body to slide freely during compression and traction.

The power to drive the reciprocating movement of the foot support platform can be provided alternatively by a conventional rack and pinion drive, a screw actuator, a hydraulic piston or a drive wheel. In addition the braking action exerted by the weight of the patient's upper body acting frictionally on the bearing pads can alternatively be provided by conventional mechanical, electrical or hydraulic brakes or by force exerted by the patient against handles attached to the frame. A preferred mode of operation of the present invention involves applying forces of equal magnitude during the compression and traction, or pushing and pulling, sequences. The magnitude of the compression and tension force applied to the patient's body depends on the force exerted on the upper body pad. Typically forces applied to the patient are in the range of ten to seventy pounds.

In view of the foregoing it is apparent that the present invention provides a therapeutic treatment machine capable of applying alternating cycles of preselected degrees of compression and traction to the back and spinal column or to other portions of a patients body.

The machine is adjustable to accommodate different torso lengths and allows the patient to control the duration, frequency and intensity of treatment. The sliding engagement between the patient and the upper body support pad combines ease of control and protection against the application of excessive forces. Safety step switches activated by any obstruction in the path of the reciprocating foot support platform prevent accidental injury to the patient or others and the use of stepped-down 12 volt AC converted to DC at the machine minimizes electrical risk. The fold-away nature of the hinged table and removable legs allows the machine to portably accompany the patient to provide treatment while traveling.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A therapeutic treatment machine for applying sequences of selected amounts of alternating tension and compression between two portions of the body of a patient comprising:

a frame having a forward section and a rearward section supported by a plurality of legs;

a pad for supporting a first body portion of a patient mounted within said forward section of said frame;

a platform for supporting and securing a second body portion of a patient displaceably mounted within said rearward section of said frame;

means for cyclically driving said platform forcefully in the forward direction and alternatingly driving said platform forcefully in the rearward direction; and means for sensing an obstruction along the forward and rearward path of said platform and deactivating said cyclical driving means immediately after sensing said obstruction.

2. The therapeutic treatment machine of claim 1 wherein said frame is hinged between said forward section and said rearward section to allow said sections to be folded together for compact storage.

3. The therapeutic treatment machine of claim 1 wherein said plurality of legs are removably mounted in said frame for compact storage.

4. The therapeutic treatment machine of claim 1 wherein said platform is mounted in said frame on bearing blocks attached to the under side of said platform slidably supported along the sides of said frame.

5. The therapeutic treatment machine of claim 1 wherein said means for cyclically driving said platform forcefully forward and rearward includes a reversible tubular motor mounted across the lower surface of said assembly non-slidingly engaged with a drive cable extending in the forward and rearward direction along said rearward frame section.

6. The therapeutic treatment machine of claim 1 further comprising means for selectively controlling the length of displacement in the forward and rearward direction of said platform.

7. The therapeutic treatment machine of claim 1 further comprising means for selectively controlling the speed of displacement in the forward and rearward direction of said platform.

8. The therapeutic treatment machine of claim 1 further comprising means for selectively adjusting the distance between said pad and said platform to accommodate the length of the patient.

9. The therapeutic treatment machine of claim 1 further comprising rotatably mounted rollers extending across said frame between said pad and said platform.

* * * * *